United States Patent [19]

Kubota et al.

[11] 4,323,684
[45] Apr. 6, 1982

[54] PROCESS FOR PREPARING A 2,2,6,6-TETRAALKYL-4-PIPERIDYL SPIRO ALIPHATIC ETHER

[76] Inventors: Naohiro Kubota, 404-1 Ageomura, Ageo; Toshihiro Shibata, 136-49-3-104 Nara-cho, Omiya, both of Japan

[21] Appl. No.: 175,487

[22] Filed: Aug. 5, 1980

[30] Foreign Application Priority Data

Aug. 8, 1979 [JP] Japan .................. 54-100916

[51] Int. Cl.³ .......................... C07D 491/13
[52] U.S. Cl. ........................................... 546/19
[58] Field of Search ............... 546/19; 260/45.8 NP, 260/45.8 NZ

[56] References Cited

U.S. PATENT DOCUMENTS

| | | | |
|---|---|---|---|
| 3,899,464 | 8/1975 | Murayama et al. | 260/45.8 NP |
| 4,096,114 | 6/1978 | Minagawa et al. | 546/19 |
| 4,105,625 | 8/1978 | Minagawa et al. | 546/19 |
| 4,115,476 | 9/1978 | Minagawa et al. | 546/19 |
| 4,116,927 | 9/1978 | Minagawa et al. | 546/16 |
| 4,118,369 | 10/1978 | Minagawa et al. | 544/224 |
| 4,124,564 | 11/1978 | Minagawa et al. | 260/45.7 R |
| 4,128,608 | 12/1978 | Minagawa et al. | 260/45.8 NZ |
| 4,136,081 | 1/1979 | Minagawa et al. | 546/19 |
| 4,250,312 | 2/1981 | Nakahara et al. | 546/19 |
| 4,250,313 | 2/1981 | Nakahara et al. | 546/19 |

*Primary Examiner*—Robert T. Bond

[57] ABSTRACT

A process is provided for the preparation of a 2,2,6,6-Tetraalkyl-4-piperidyl spiro aliphatic ether represented by the formula

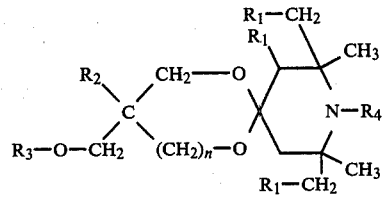

in which $R_1$ is a hydrogen atom or an alkyl group having 1 to 4 carbon atoms, $R_2$ is a hydrogen atom, or a methyl, ethyl, or hydroxymethyl group, n is zero or one, $R_3$ is a group represented by a formula

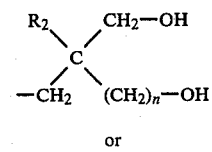

or

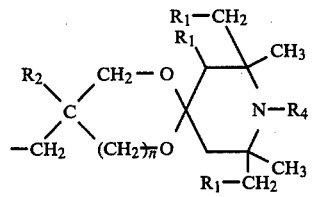

and $R_4$ is a hydrogen atom or an alkyl group, by the reaction of a 2,2,6,6-tetraalkyl-4-piperidone compound represented by the formula

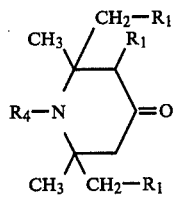

or an acid addition salt thereof with an oxybis (alkanediol) compound represented by the formula

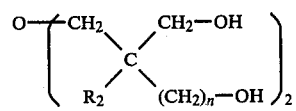

10 Claims, No Drawings

PROCESS FOR PREPARING A 2,2,6,6-TETRAALKYL-4-PIPERIDYL SPIRO ALIPHATIC ETHER

BACKGROUND OF THE INVENTION

This invention relates to certain 2,2,6,6-tetraalkylpiperidine compound stabilizers for synthetic polymers and to an improved process for their preparation.

Many 2,2,6,6-tetraalkylpiperidine compound stabilizers are known. For a summary of the art, M. Minagawa et al. U.S. Pat. No. 4,124,564 of Nov. 7, 1978 can be consulted at column 1 line 15 to column 2 line 45. In particular, hindered piperidine alcohol compounds having Formula A, which can be named 2,2,6,6-tetramethyl-4-piperidone spiroketal carbinol compounds, or more systematically 9-aza-3-hydroxymethyl-3-alkyl-8,8,10,10,-tetramethyl-1,5-dioxaspiro(5,5) undecanes,

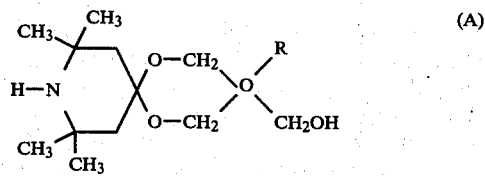

have been disclosed by K. Murayama in U.S. Pat. No. 3,899,464 of Aug. 12, 1975 as stabilizers able to protect syntheticpolymers and plastics against the harmful effects of exposure to ultraviolet radiation and heat. Compounds of Formula A have also been disclosed to be valuable synthetic intermediates for the preparation of even better stabilizers by reaction of the compounds at the alcoholic hydroxyl group to form various derivatives. Outstandingly effective stabilizers among these derivatives are certain organic phosphite esters disclosed by M. Minagawa et al in U.S. Pat. No. 4,096,114 of June 20, 1978; hydroxyaliphatic dicarboxylic and tricarboxylic acid esters disclosed by M. Minagawa et al in U.S. Pat. No. No. 4,105,625 of Aug. 8, 1978; diol bis-carbonate esters disclosed by M. Minagawa et al in U.S. Pat. No. 4,115,476 of Sept. 19, 1978; butane-and butenetricarboxylic acid esters disclosed by M. Minagawa et al in U.S. Pat. No. 4,116,927 of September 1978; heterocyclic carboxylic acid esters disclosed by M. Minagawa et al in U.S. Pat. 4,118,369 of Oct. 3, 1978; and aliphatic tetracarboxylic acid esters disclosed by M. Minagawa et al in U.S. Pat. No. 4,136,081 of Jan. 23, 1979.

M. Minagawa et al. in U.S. Pat. No. 4,128,608 of Dec. 5, 1978 disclosed a class of 2,2,6,6-tetramethyl-4-piperidyl spiro aliphatic ether stabilizers having the general formula

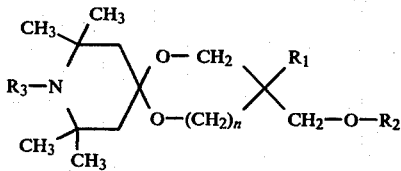

wherein
$R_1$ is selected from the group consisting of hydrogen, lower alkyl and lower hydroxyalkyl having one or two carbon atoms;

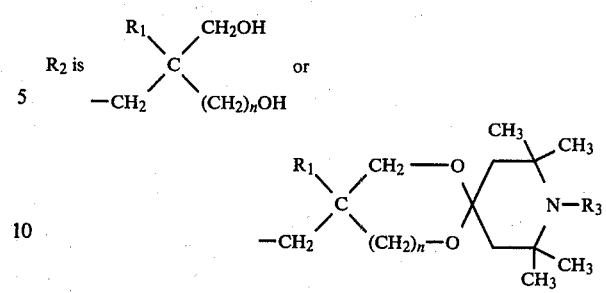

$R_3$ is selected from the group consisting of hydrogen and O; and n is 0 or 1.

Minagawa et al. disclosed preparation of these compounds by an acidcatalyzed condensation reaction in non-polar organic solvents such as benzene and toluene.

SUMMARY OF THE INVENTION

In accordance with this invention, a process for the preparation of a 2,2,6,6-tetraalkyl-4-piperidylspiro aliphatic ether represented by the formula 1

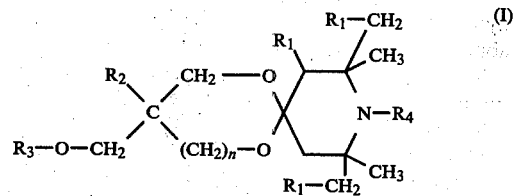

or an acid addition salt thereof, in which $R_1$ is a hydrogen atom or an alkyl group having 1 to 4 carbon atoms, $R_2$ is a hydrogen atom, or a methyl, ethyl, or hydroxymethyl group, n is zero or one, $R_3$ is a group represented by a formula

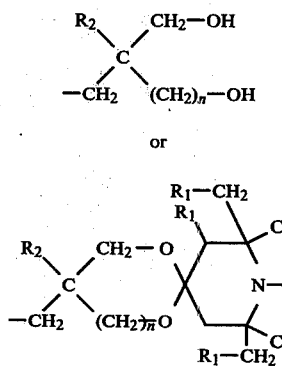

and $R_4$ is a hydrogen atom, an aralkyl group, or an alkyl group, by the reaction of a 2,2,6,6-tetraalkyl-4-piperidone compound represented by the formula 11

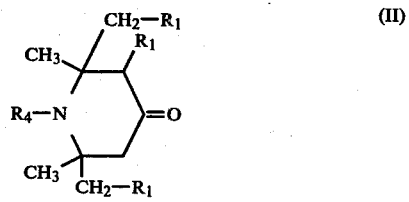

or an acid addition salt thereof with an oxybis(alkanediol) compound represented by the formula 111

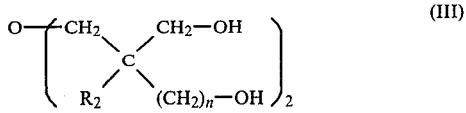

(III)

is improved in speed of reaction, yield of product, and purity of product obtained, by carrying out the reaction of the 2,2,6,6-tetraalkyl-4-piperidone compound and the oxybis(alkanediol) compound in the presence of a polar solvent selected from the group consisting of alcohols having 1 to 13 carbon atoms and 1 to 3 alcoholic hydroxyl groups, amides of phosphoric acid, carbonic acid, and carboxylic acids having 1 to 4 carbon atoms, and chlorobenzenes having 1 to 2 chlorine atoms.

DESCRIPTION OF THE PREFERRED EMBODIMENTS

In the above formulas, (1), (11) and (111), the $R_1$ alkyl group can be methyl, ethyl, propyl, isopropyl, n-butyl, sec-butyl, and t-butyl, the $R_4$ group can be any of these alkyls as well as pentyl, hexyl, octyl, 2-ethylhexyl, benzyl, phenylethyl, trimethylbenzyl and the like up to about 15 carbon atoms.

The acids constituting the acid addition salt of compound (1) or (11) can be hydrochloric acid, sulfuric acid, phosphoric acid, p-toluenesulfonic acid, acetic acid and oxalic acid. Many compounds represented by formula 1 that can be prepared by the process of this invention are disclosed by M. Minagawa et al in U.S. Pat. No. 4,128,608 of Dec. 5, 1978. The specific compounds disclosed by M. Minagawa in this patent at column 8 lines 1 to 60 are here incorporated by reference.

Exemplary polar solvents which can be used in this invention are monohydric aliphatic alcohols such as methyl, ethyl, propyl, isopropyl, n-butyl, sec-butyl, tert-butyl, n-amyl, tert-amyl, isoamyl, hexyl, isohexyl, heptyl, octyl, isooctyl, 2-ethylhexyl, n-decyl, isodecyl, lauryl, and tridecyl alcohols; cycloaliphatic alcohols such as cyclopentanol, cyclohexanol, cyclooctanol, cyclododecanol and 4-methylcyclohexanol; aryl substituted alcohols such as benzyl, 2-phenylethyl, 3-phenylpropyl and 2-phenylpropyl alcohols; oxygen heterocyclic alcohols such as, tetrahydrofurfuryl-, 5-methyltetrahydrofurfuryl- and α-methyltetrahydrofurfuryl-alcohol; glycols and ether-glycols such as propylene glycol, ethylene glycol and diethylene glycol; monohydric ether alcohols having 1 to 2 ether groups such as methyl, ethyl, isopropyl, butyl, isobutyl, hexyl, cyclohexyl and phenyl monoethers of ethyleneglycol and the methyl, ethyl, isopropyl, butyl and isobutyl monoethers of diethylene glycol; triethyleneglycol monoalkylethers such as triethyleneglycol-monomethylether, -monoethylether and monobutylether; glycerol derivatives such as glycerol, glycerol-1,2-dimethylether, -1,3-dimethylether, -1,3-diethylether and -1-ethyl-2-propylether; amides of phosphoric acid, carbonic acid, and carboxylic acids having 1 to 4 carbon atoms such as formamide, methylformamide, dimethylformamide (DMF), diethylformamide (DEF), acetamide, methylacetamide, dimethylacetamide (DMA), urea N-methylurea, N,N-diethylurea N,N-dimethylurea, N-methylpyrrolidone, tetramethylurea and hexamethylphosphor(tri) amide and halogenated aromatic hydrocarbons such as chlorobenzene and o-dichlorobenzene. Mixtures of these polar solvents can also be used.

The polar solvent or solvent mixture is liquid at the reaction temperature where it is used, and can be liquid or solid at room temperature. Non polar solvents can also be used together with the polar solvents. When a non-polar solvent is used, the weight ratio of polar solvent to non-polar solvent in the reaction mixture is at least 1:2, preferably at least 1:1.

Exemplary non polar solvents are hydrocarbons such as benzene, toluene, xylene, ethylbenzene, cumene, pseudocumene, cymene, hexane, heptane, octane, liquid paraffin and mineral spirit; and ethers such as diethylether, tetrahydrofuran, dioxane, 1,2-dimethoxyethane and bis(2-methoxyethyl)ether.

Water produced as a by-product of the reaction in which the spiro alkylether is produced is suitably removed as an azetrope with a hydrocarbon such as toluene, xylene, hexane and octane as the reaction proceeds. Alternatively, reaction water can be allowed to accumulate in the mixture and removed during isolation of the product.

In the process of this invention the use of an acid catalyst is preferred to complete the reaction quickly. Concentration of acid catalyst in the reaction mixture can range from about 0.01% to about 10% by weight. Suitable acid catalysts include hydrochloric acid, sulfuric acid, phosphoric acid and p-toluenesulfonic acid, and other acids having in a 1% aqueous solution a pH not greater than 3.

The process of this invention is suitably carried out at any convenient temperature in the range from 20° to 300° C., preferably in the range from 60° to 200° C.

The process of this invention can be conveniently carried out at atmospheric pressure or less than atmospheric pressure.

The invention is further illustrated without limitation by the following preparations of bis(3-hydroxymethyl-7,7,9,9-tetramethyl-8-aza-1,5-dioxa spiro (5,5)-3-undecylmethyl)ether.

CONTROL 1—1

19.2 g (0.10 mole) of 2,2,6,6-tetramethyl-4-piperidone hydrochloride, 12.7 g (0.05 mole) of dipentaerythritol and 1.0 g of p-toluenesulfonic acid were dispersed into a mixture of 95 ml of toluene and 5 ml of n-hexane and the produced water was removed under reflux for 16 hrs. Then, the reaction mixture was cooled and neutralized with 40% KOH aq.. Then toluene was added and the organic layer was washed with saturated aqueous NaCl solution, dried, and concentrated by evaporation. 11.1 g (crude yield 42%) of viscous brown oil was obtained. The compound was identified by the following analysis. Amine value: found. 5.27% calcd. 5.30% I.R.: $\nu_{NH}$3240 cm$^{-1}\nu_{c-o}$(ketal)1100 cm$^{-1}$ purity: 94% (calculated from the proportion of peaks with high speed liquid chromatography) proportion of reacted dipentaerythritol: 51% (calculated from the amount of recovered dipentaerythritol)

EXAMPLE 1-1

The preparation of the 4-piperidone spiroketal alkyl ether compound as in Control 1-1 was repeated using a mixed solvent of cyclohexanol/toluene (95:5) in place of that of toluene/n-hexane (95:5). 24.8 g (crude yield 94%) of viscous brown oil was obtained.

Amine value: found. 5.28% calcd. 5.30% I.R.: $\nu_{NH}$3240 cm$^{-1}\nu_{c\text{-}o}$(ketal)1100 cm$^{-1}$ purity: 99%. proportion of reacted dipentaerylthritol: 99%.

Comparison of the results of Control 1—1 and Example 1—1 according to this invention shows the unexpected and dramatic improvement brought about by use of the polar solvent in Example 1—1.

Controls 1-2, 1-3 and Examples 1-2 to 1-8

Preparations of the same 4 piperidone spiroketal alkylether as in Control 1—1 and Example 1—1 were carried out using several solvent systems in place of the solvent system of toluene/n-hexane (95:5).

The solvent systems, reaction conditions and results are shown in Table 1.

EXAMPLES 2-1 to 2-5

Several 4-piperidone spiroketal alkylether compounds having the formula (IV) were prepared.

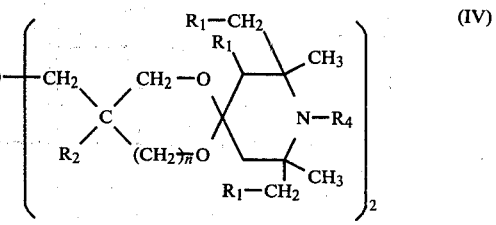

(IV)

TABLE 1

Preparation of Bis(3-hydroxymethyl-7,7,9,9-tetramethyl-8-aza-1,5-dioxaspiro (5,5)-3-undecylmethyl) ether

| No. | Solvent system (weight ratio) | reaction time hr | reaction temperature max °C. | Proportion of reacted dipentaerythritol | Product yield (crude) % | Product purity % |
|---|---|---|---|---|---|---|
| Control | | | | | | |
| 1-1 | toluene/n-hexane (95/5) | 16 | 108 | 51 | 42 | 94 |
| 1-2 | benzene/toluene (60/40) | 17 | 98 | 54 | 47 | 95 |
| 1-3 | liquid paraffin (100) | 20 | 140 | 48 | 40 | 94 |
| Example | | | | | | |
| 1-1 | cyclohexanol/ toluene (95/5) | 1 | 142 | 99 | 94 | 99 |
| 1-2 | sec-butanol/ hexane (95/5) | 2 | 104 | 95 | 88 | 98 |
| 1-3 | sec-butanol (100) | 4 | 102 | 91 | 84 | 97 |
| 1-4 | DMF/toluene (60/40) | 3 | 110 | 94 | 90 | 99 |
| 1-5 | 2(2'-butoxyethoxy)ethanol & toluene (90/10) | 2 | 164 | 96 | 87 | 97 |
| 1-6 | 2-methoxyethanol + n/octane (80/20) | 2 | 128 | 94 | 86 | 98 |
| 1-7 | 2-ethylhexanol/ DMA/n-heptane (35/35/30) | 3 | 152 | 95 | 92 | 98 |
| 1-8 | DEF (100) | 5 | 181 | 92 | 88 | 99 |

DMF = N,N-dimethylformamide; DEF = N,N-diethylformamide

The tabulated results show the unexpected superiority of the process of this invention in giving greater yields of higher purity product in much less time than the control procedure. The results also show that the improvement obtained according to this invention is independent of the reaction temperature.

The compounds in Controls 2-1 to 2—2 were prepared in a mixed solvent of xylene and toluene (weight ratio (90/10) and the compounds in Examples 2-1 to 2-5 were prepared in a mixed solvent of cyclohexanol and toluene (weight ratio 90/10).

The results are shown in Table 2.

TABLE 2

| | [IV] Compound | | | | Reaction time | Proportion of reacted dipentaerythritol % | Product Yield (crude) | Product Purity % |
|---|---|---|---|---|---|---|---|---|
| No. | R$_1$ | R$_2$ | R$_4$ | n | hr | | | |
| Control | | | | | | | | |
| 2-1 | H | C$_2$H$_5$ | H | 1 | 10 | 82 | 74 | 75 |
| 2-2 | CH$_3$ | C$_2$H$_5$ | H | 1 | 9 | 74 | 65 | 70 |
| Example | | | | | | | | |
| 2-1 | H | C$_2$H$_5$ | H | 1 | 2 | 95 | 90 | 96 |

TABLE 2-continued

| No. | [IV] Compound R$_1$ | R$_2$ | R$_4$ | n | Reaction time hr | Proportion of reacted dipentaerythritol % | Product Yield (crude) | Product Purity % |
|---|---|---|---|---|---|---|---|---|
| 2-2 | H | H | H | 0 | 1 | 99 | 96 | 99 |
| 2-3 | H | CH$_2$OH | CH$_3$ | 1 | 4 | 96 | 95 | 98 |
| 2-4 | CH$_3$ | C$_2$H$_5$ | H | 1 | 3 | 92 | 88 | 93 |
| 2-5 | C$_2$H$_5$ | CH$_3$ | CH$_3$ | 1 | 4 | 95 | 92 | 93 |

These results show the unexpected superiority of the process of this invention in the preparation of a variety of 2,2,6,6-tetraalkyl-4-piperidyl spiro aliphatic ethers in high yield and purity.

We claim:

1. In a process for preparing a 2,2,6,6-tetraalkyl-4-piperidyl spiro aliphatic ether compound represented by the formula

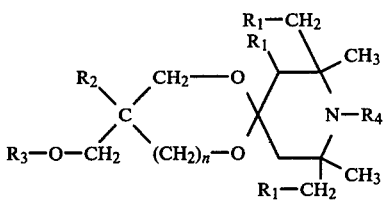

or an acid addition salt thereof, in which R$_1$ is a hydrogen atom or an alkyl group having 1 to 4 carbon atoms, R$_2$ is a hydrogen atom, or a methyl, ethyl, or hydroxymethyl group, n is zero or one, R$_3$ is a group represented by a formula

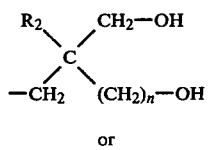

or

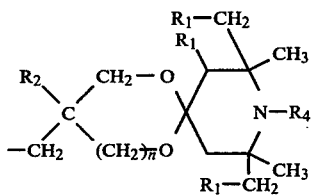

and R$_4$ is a hydrogen atom or an alkyl group, comprising the reaction of a 2,2,6,6-tetraalkyl-4-piperidone compound represented by the formula

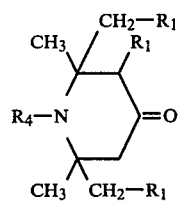

or an acid addition salt thereof with an oxybis (alkanediol) compound represented by the formula

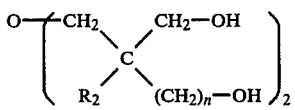

in which reaction water is formed, the improvement comprising carrying out the reaction of the 2,2,6,6-tetraalkyl-4-piperidone compound and the oxybis (alkanediol) compound in the presene of a polar solvent selected from the group consisting of alcohols having 1 to 13 carbon atoms and 1 alcoholic hydroxyl group, and amides of carboxylic acids having 1 to 4 carbon atoms.

2. A process according to claim 1 carried out in the presence of an acid catalyst.

3. A process according to claim 1 in which the polar solvent is a monohydric alcohol.

4. A process according to claim 3 in which the polar solvent is an aliphatic ether alcohol having 1 to 2 ether groups.

5. A process according to claim 1 in which the polar solvent is N,N-diethylformamide.

6. A process according to claim 1 in which R$_1$ and R$_4$ are hydrogen atoms.

7. A process according to claim 1 in which R$_1$ is a methyl or ethyl group.

8. A process according to claim 1 in which R$_4$ is a methyl group.

9. A process according to claim 1 in which R$_2$ is a methyl or ethyl group.

10. A process according to claim 1 in which R$_2$ is a hydroxymethyl group.

* * * * *

UNITED STATES PATENT AND TRADEMARK OFFICE
CERTIFICATE OF CORRECTION

PATENT NO. : 4,323,684
DATED : April 6, 1982
INVENTOR(S) : Naohiro Kubota et al

It is certified that error appears in the above—identified patent and that said Letters Patent are hereby corrected as shown below:

In the Abstract: At the end, please insert --carried out in the presence of a polar solvent.--
Column 1, line 31 :"syntheticpolymers" should be -- synthetic polymers--
Column 4, line 2 : "solvants" should be --solvents--.

Signed and Sealed this

Twenty-fourth Day of September 1985

[SEAL]

Attest:

Attesting Officer

DONALD J. QUIGG

Commissioner of Patents and
Trademarks—Designate